United States Patent [19]
Chimenti et al.

[11] Patent Number: 5,404,015
[45] Date of Patent: Apr. 4, 1995

[54] METHOD AND SYSTEM FOR CONTROLLING AND OPTIMIZING ISOMERIZATION PROCESSES

[75] Inventors: Robert J. L. Chimenti, Short Hills; Gerald M. Halpern, Bridgewater, both of N.J.

[73] Assignee: Exxon Research & Engineering Co., Florham Park, N.J.

[21] Appl. No.: 125,062

[22] Filed: Sep. 21, 1993

[51] Int. Cl.$^6$ .................. G01N 21/35; G01N 33/28
[52] U.S. Cl. ................. 250/339.12; 250/343; 356/436
[58] Field of Search ........... 250/339, 340, 341, 339.12, 250/339.01, 339.06, 343; 356/436

[56] References Cited

U.S. PATENT DOCUMENTS

| | | |
|---|---|---|
| 4,701,838 | 10/1987 | Swinkels et al. . |
| 4,800,279 | 1/1989 | Hieftje et al. . |
| 4,804,802 | 2/1989 | Evans et al. .................. 585/734 |
| 4,963,745 | 10/1990 | Maggard . |
| 5,046,846 | 9/1991 | Ray et al. . |
| 5,082,985 | 1/1992 | Crouzet et al. .................. 585/501 |
| 5,145,785 | 9/1992 | Maggard et al. ............. 250/339 X |
| 5,223,714 | 6/1993 | Maggard .................. 250/339 X |
| 5,243,546 | 9/1993 | Maggard . |

FOREIGN PATENT DOCUMENTS

| | | |
|---|---|---|
| 0285251B1 | 10/1988 | European Pat. Off. . |
| 304230 | 2/1989 | European Pat. Off. ....... 250/339.12 |
| 0304232A3 | 2/1989 | European Pat. Off. . |
| 0304233A1 | 2/1989 | European Pat. Off. . |
| 0305090B1 | 3/1989 | European Pat. Off. . |
| 0328826B1 | 8/1989 | European Pat. Off. . |
| 0368560A3 | 5/1990 | European Pat. Off. . |
| 52-22978 | 2/1977 | Japan .................. 356/436 |
| 9115762 | 10/1991 | WIPO . |
| 9324823 | 12/1993 | WIPO . |

OTHER PUBLICATIONS

Evans et al. 'Determination of Carbon-Hydrogen Groups in High Molecular Weight Hydrocarbons', Anal. Chem., vol. 23, No. 11, 1951, pp. 1604–1610.

*Primary Examiner*—Constantine Hannaher
*Assistant Examiner*—Edward J. Glick
*Attorney, Agent, or Firm*—Ronald D. Hantman

[57] ABSTRACT

The present invention is a method to determine the oil content of a waxy isomerate by NIR radiation which is then used to control the separation of oil from the waxy isomerate.

19 Claims, 3 Drawing Sheets

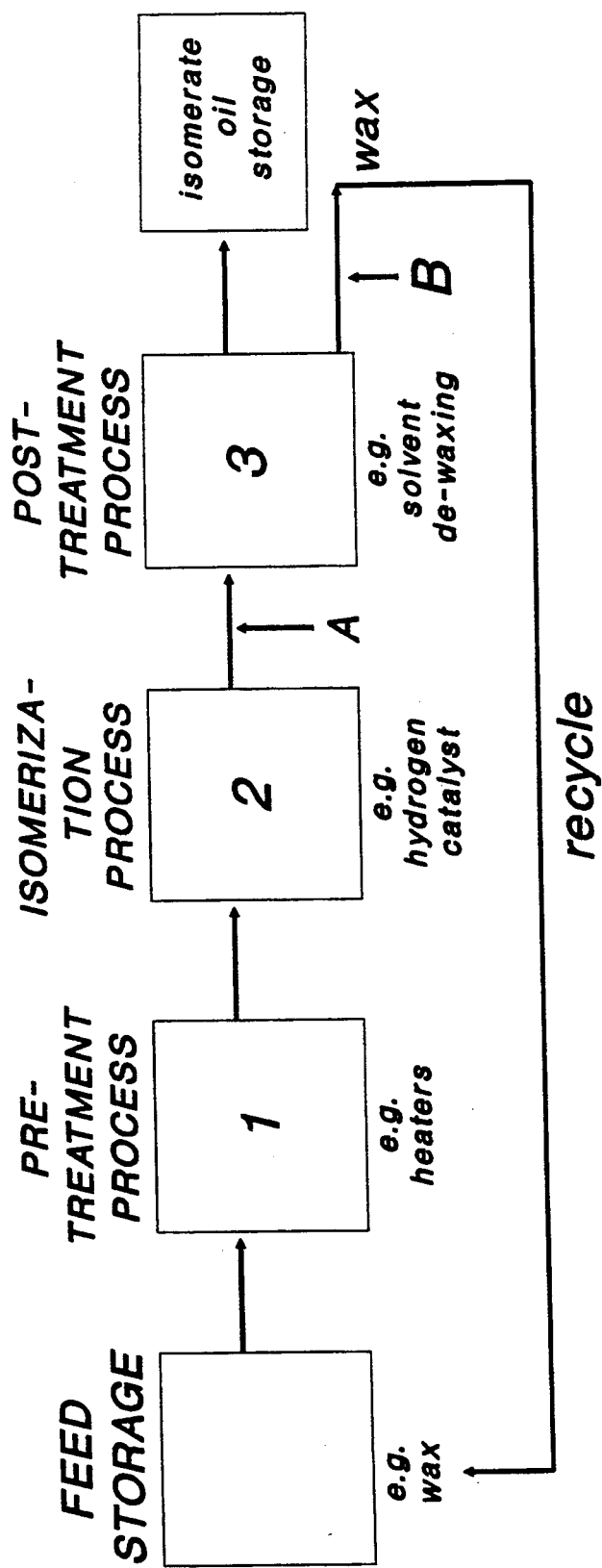

METHOD AND SYSTEM FOR CONTROLLING AND OPTIMIZING ISOMERIZATION PROCESSES

BACKGROUND OF THE INVENTION

The present invention is a system and method to control and optimize isomerization processes.

Such processes include the isomerization of a hydrocarbon feed to create a product (i.e., isomerate) whose economic value exceeds that of the feed material. Isomerization is generally carried out with a catalyst and under reaction conditions chosen to maximize conversion consistent with target product specifications. Plant operating strategies attempt to maximize the production of isomerate product within certain constraints such as feed rates, catalyst lifetimes, process parameters (e.g., temperature and pressure), and desired product properties which may be dependent upon the degree of conversion. Process models are sometimes developed and employed which permit the plant operator to optimize run lengths; thereby achieving maximum profitability within the practical constraints. Typically, the process is allowed to run for a predetermined time, either continuous or batch, established by experience and model calculations. This predetermined time (i.e., run-length) is not always optimum due to feed variability, imperfections in the process model and uncertainties in catalyst activity and actual process conditions. The net result is that the process may be terminated prematurely, or allowed to proceed longer than would be optimum. In the first instance, profitability is diminished since the catalyst and the capital-intensive plant equipment are not fully utilized. In the second instance, for example, by allowing the process to run for a time longer than is optimum, feed material will not be adequately converted into valuable isomerate product when the catalyst has exceeded its useful lifetime. The net result is the unwanted production of lesser-valued material which, when blended with the higher-valued material produced during the early stages of the run, reduce the quality (i.e., net value) of the final product. Additionally, storage costs are incurred for products having off-target specifications.

For the above stated reasons, there is significant economic advantage to be gained by operating isomerization processes under a control scheme which includes means to continuously monitor the process stream and estimate, from this input, the quality of the product or the effectiveness of the process, or both as a function of time. This control scheme comprises, in part, an analyzer that would initially monitor and analyze the first batch of product and a means for said analyzer to send a signal either to a computer or to a plant operator confirming that the process is yielding product with maximum available quality. For example, the analyzer would measure the degree to which feed has been converted to isomerized product (i.e., degree of conversion). As feed quality, process conditions, and catalyst activity vary due to either known or unknown causes, the analyzer will monitor the effectiveness of the conversion process and provide a signal to either a computer or a process operator that the run should be terminated. One object of the present invention is to provide process units with a means capable of determining the degree of conversion in an isomerization application, or other applications where plant economics can be optimized by continuously tracking the quality of the product.

Another aspect of the isomerization process is the separation of the isomerate product from the non-isomerized feed. Incomplete separation results in loss in yield of the higher valued isomerate, since the separated, non-isomerized feed is recycled and mixed with fresh feed. Consequently, means to determine the effectiveness of the separation and to control the separation process based upon this information has value and is another application of this invention to the isomerization system.

One specific, but not restrictive example of such a process involves the isomerization of a linear paraffin feed into a product consisting mainly of branched paraffins. More specifically, if the linear paraffins are of sufficiently high molecular weight, the feed will be a wax and the isomerate product will be an oil over a broad temperature range. For example, the feed may be a hydrocarbon which boils in the lubricating oil range. In this case, all of the above general arguments apply—the wax is catalytically isomerized into a higher-value isomerate oil. The analyzer described in the present invention provides information on the degree of conversion which, in this case, is directly determined by the relative amount of branched versus linear paraffins in the product. Complete conversion is rarely achieved in practice; hence, the product of the isomerization process acting upon a hydrocarbon wax feed, for example, will contain some unconverted wax. Thus, the product mixture is called a waxy isomerate. Since complete conversion is not achieved in practice, the analyzer will be used to maximize run-length and optimize process operations by reporting either to a computer or a process operator when the relative proportion of branched to linear paraffins has maximized. A plant optimization scheme could use this information, for example, to decide when to terminate the run; say at the time that the analyzer shows that the abundance of branched versus linear paraffins has either leveled-out, or shows the first signs of decline or to optimize operating conditions such as temperature and $H_2$ pressure.

Since conversion of the wax to isomerate oil is not complete in practice it is necessary to separate the isomerate oil from the non-isomerized wax. This may be accomplished by catalytic or solvent dewaxing of the mixture. Two streams will emerge from the dewaxer, a dewaxed isomerate oil and a residual wax stream. The residual wax stream may contain some of the isomerate oil since the dewaxing process is also not complete, in practice. For example, in solvent dewaxing isomerate oil may be physically entrained in the wax. In this example, the efficiency of the separation process may be controlled by solvent type and amount relative to the wax-isomerate mixture feed, and flow rate to the separation filter. Means to provide rapid determination of the amount of the isomerate oil that may be entrained in the wax allows the operator to control and optimize the dewaxing process with respect to the reduction of isomerate oil yield and throughput.

The present invention claims a method for controlling and optimizing such processes as are typified but are not limited to isomerization processes in general and wax isomerization processes specifically. The present invention also claims a method which is both novel and unobvious whereby the quality of an isomerization process can be determined by spectroscopic means.

SUMMARY OF THE INVENTION

The present invention includes a system and method to determine the oil content of waxy isomerates. This allows for controlling and optimizing an isomerization process and system. The method includes the steps of irradiating a hydrocarbon feed stream including waxy isomerates and oil with near-infrared radiation, that is, radiation having wavelength in the range from 700 nm to 2800 nm, and determining the optical absorptivity of the hydrocarbon feed stream at least one selected wavelength in this range, and, determining the weight percent of the oil content of the oil and wax mixture, comprising the waxy isomerate, from the difference in the optical absorptivity.

The method is used in a system to optimize an isomerization process.

In a preferred embodiment, the difference in absorptivity between two wavelengths is used in order to minimize possible errors (discussed below).

In a preferred embodiment, the two selected wavelengths are about 1210 nm and 1196 nm or about 927 nm and 916 nm.

BRIEF DESCRIPTION OF THE DRAWINGS

FIG. 3 shows, schematically, a wax isomerization system which is comprised of wax pretreatment, isomerization, and waxy-isomerate post-treatment processes.

DESCRIPTION OF THE PREFERRED EMBODIMENT

The present invention is a system and method to determine the oil content of waxy isomerates by near-infrared (NIR) absorbance spectroscopy. This NIR method can replace the laboratory ASTM test and can be implemented in an on-line analyzer for process monitoring and control of the isomerate oil yield.

Figure 1:
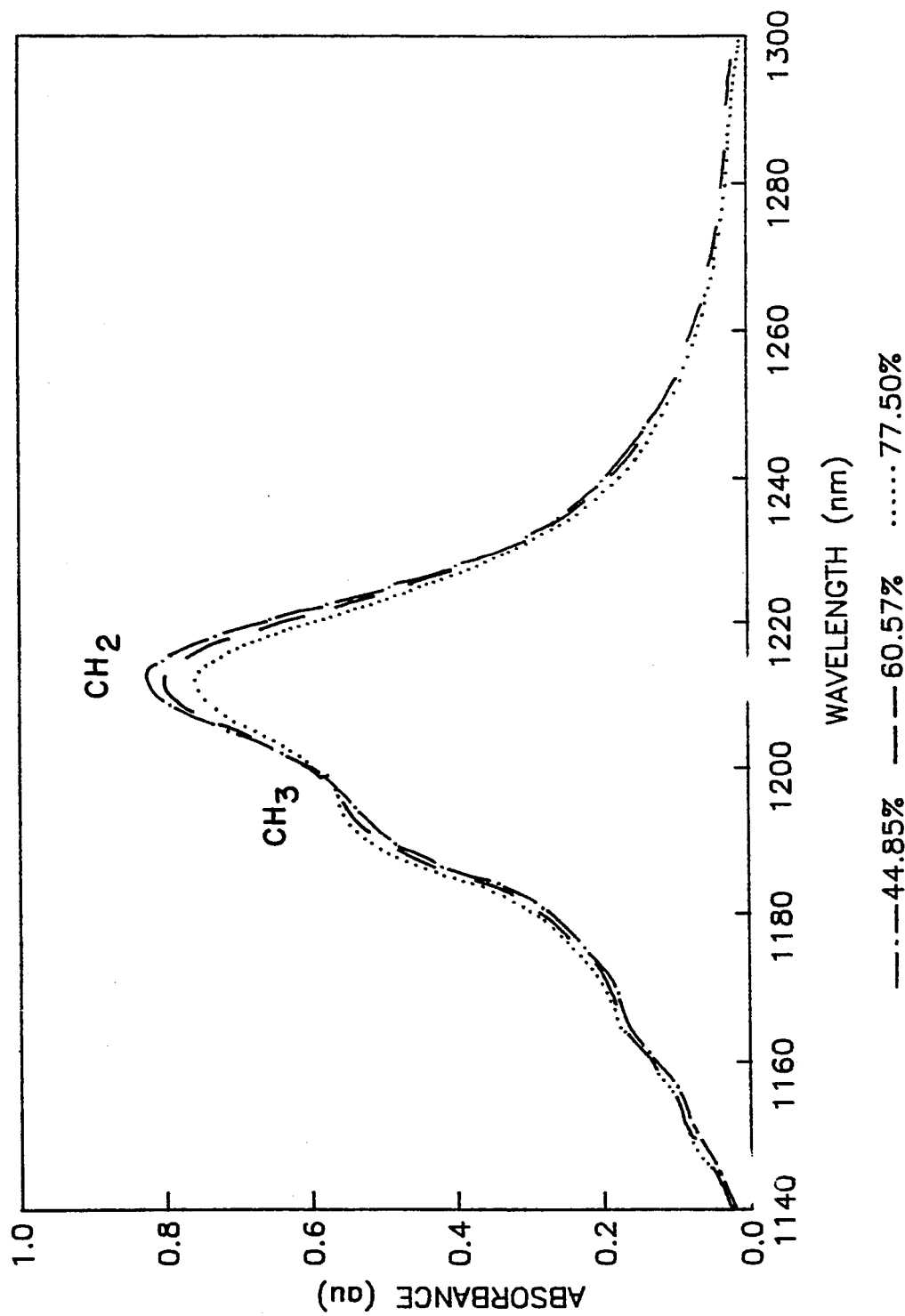
FIG. 1 shows the absorption of isomerates containing oil for three samples.

The method and system uses the difference between the absorptivity of NIR radiation at two different wavelengths to determine the oil content of waxy isomerates. The absorptivity is defined as the negative of the logarithm of the ratio of the transmitted to incident intensity, the logarithm being divided by the pathlength through which the radiation traversed. The two wavelengths used in the present invention correspond to the near-IR overtone features of the $CH_3$ and $CH_2$ stretching vibrational modes, whose peaks are at, approximately, 1196 and 1210 nm, respectively. These wavelengths are chosen because the isomerate oil consists largely of branched paraffins rich in $CH_3$ groups, while the isomerate wax consists largely of linear paraffins rich in $CH_2$ groups. The spectra in FIG. 1 show the absorbance of a high (77.50%), medium (60.57%), and low (44.85%) oil content isomerates in the wavelength region of 1140 nm to 1300 nm. It can be seen that the $CH_3$ feature at 1196 nm increases in relation to the $CH_2$ feature at 1210 nm with increasing oil content. The invention employs the fact that oil and wax content vary inversely.

We have shown that the ASTM oil content is a linear function of the difference between the absorptivity at the characteristic wavelengths for these groups [i.e., A(1196)−A(1210) or its negative]. In addition, using two wavelengths has the advantage of removing offsets in the spectra due, for example, to scattering or other non-absorptive phenomena is gained.

Full spectra and multivariate techniques could be employed, if needed, to improve further the accuracy and robustness of the model.

EXAMPLE - Determination of oil content of waxy isomerates

A calibration model using the absorptivity at two wavelengths in the near-IR was developed. The absorptivities, A(1210) and A(1196), at 1210 and 1196 nm, respectively, were used to predict the oil content, determined by modified ASTM method, using the model:

predicted wt %
oil = 164.796 + 441.052*[A(1196)-A(1210)]

Figure 2:
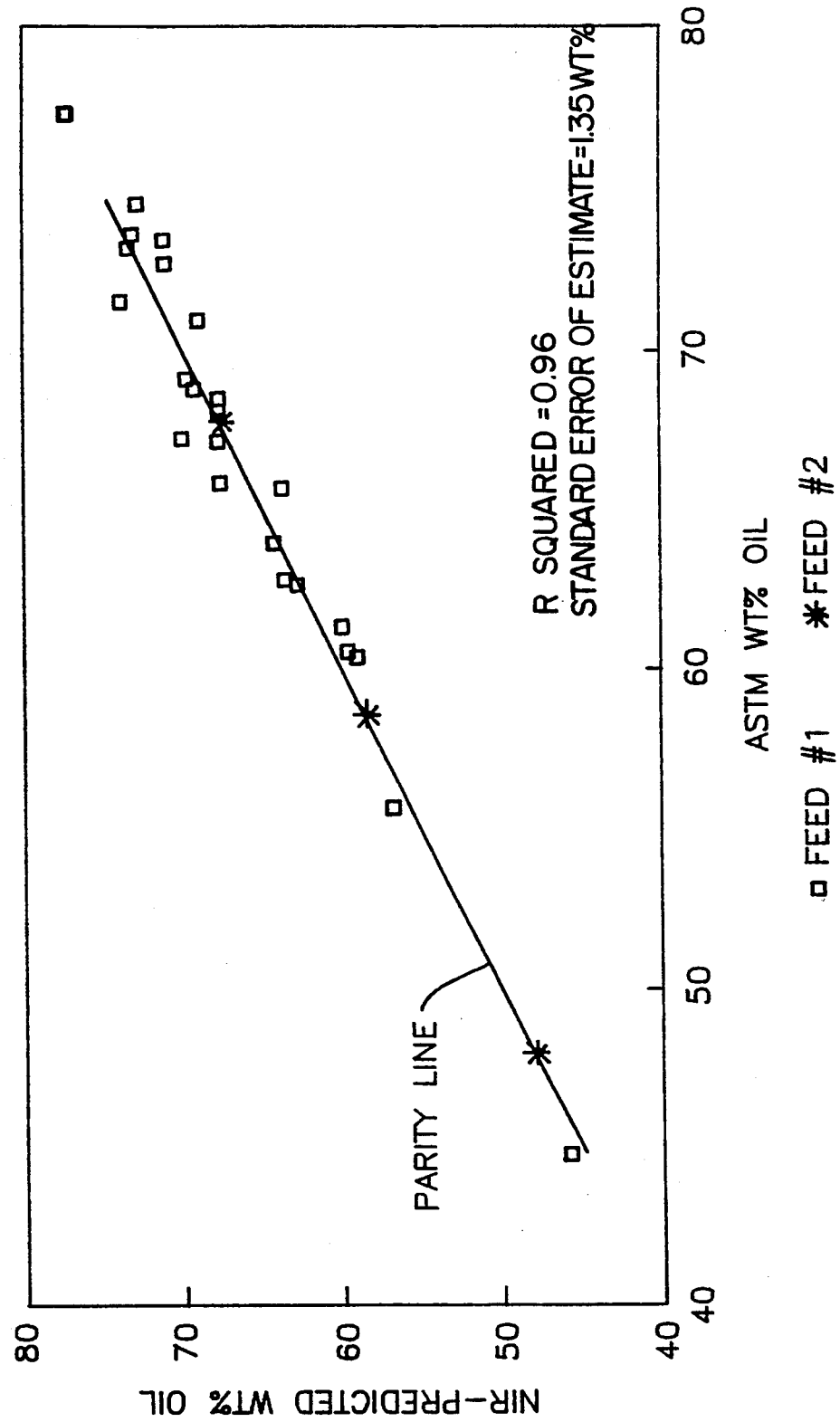
FIG. 2 shows a parity plot for the oil content of 28 samples comparing the spectrally predicted oil content to the content determined by the ASTM method.

The calibration is based upon 28 samples from the same feed. Absorbance spectra with a common pathlength of 1 cm, were taken with the samples heated to about 85° C. to insure a well mixed, single continuous phase. This calibration model successfully predicted the oil contents of three isomerates from one or more different feeds, whose spectra were not included in the set of spectra used for calibration. The correlation coefficient of the above model, $R^2 = 0.9611$ and the standard error of estimate = 1.35 wt %. The parity plot in FIG. 2 shows the NIR-predicted versus ASTM oil contents in the range 44.45 to 77.65%, for all 31 isomerate samples.

Referring to FIG. 3, wax feed may be pretreated in process 1. An example of such pretreatment is the heating of the wax to a temperature above its melting point. The molten wax is pumped into the isomerization process 2, where it contacts hydrogen and catalyst. The hydrogen, fluid flow rates, and temperature are maintained at such values so as to optimize the isomerization of the wax into an isomerate oil while maximizing catalyst life and minimizing energy costs.

The waxy isomerate, comprising a mixture of the isomerate oil and non-isomerized wax feed, is pumped into a post-treatment process 3, which may be, for example, a solvent dewaxing process to separate the wax from the isomerate oil.

The invention may be applied to several points in the wax isomerization system, two of which are labeled, A and B, in FIG. 3.

When applied to point A, the oil content, hence the degree of conversion, may be estimated by the NIR method and this estimate may be used to control the parameters of process 2. These estimates may also be used to determine when the catalyst activity has deteriorated. Finally, the estimate may be used to feed information forward to control the dewaxer comprising process 3.

When applied to point B, the oil content of the residual wax stream separated from the isomerate oil may be estimated. This estimate may be used to control the parameter of the dewaxing process 3, such as the solvent to oil ratio or the dewaxing temperature.

What is claimed is:

1. A method to determine isomerate oil content of a hydrocarbon feedstream including a mixture of isomerate oil and wax comprising the steps of:
   (a) irradiating said feedstream with optical radiation;
   (b) determining the optical absorptivity of said feedstream for at least one selected wavelength; and
   (c) determining the weight percent of said isomerate oil content from said optical absorptivity.

2. The method of claim 1 wherein said method includes determining the optical absorptivity at a second selected wavelength, and determining the difference in the optical absorptivity between said two wavelengths.

3. The method of claim 2 wherein said two selected wavelengths are about 1210 nm and 1196 nm.

4. The method of claim 2 where said two selected wavelengths are about 927 nm and 916 nm.

5. The method of claim 1 wherein said feedstream consists of a mixture of isomeric oil and wax feed.

6. A method for optimizing operating parameters for the catalytic isomerization of a hydrocarbon feedstream comprising the steps of:
   (a) feeding a molten substantially waxy feedstream into one or more catalytic reactors with catalyst and hydrogen which under operating conditions isomerizes normal paraffins in said feedstream;
   (b) irradiating the stream emerging from said catalytic reactor with near-infrared radiation;
   (c) determining the optical absorptivity of said emerging stream for at least one selected wavelength;
   (d) determining from said optical absorptivity the degree of isomerization; and
   (e) controlling at least one of the operating parameters in response to said determined degree of isomerization to optimize the catalytic isomerization.

7. The method of claim 6 wherein said method includes determining the optical absorptivity at a second selected wavelength, and determining the difference in the optical absorptivity between said two wavelengths.

8. The method of claim 7 wherein said two selected wavelengths are about 1210 nm and 1196 nm.

9. The method of claim 7 where said two selected wavelengths are about 927 nm and 916 nm.

10. A method for optimizing operating parameters for a dewaxing process comprising the steps of:
    (a) feeding a molten mixture of isomerate oil and wax feed into a dewaxer which under operating conditions separates said mixture into an isomerate oil stream and a residual wax stream;
    (b) irradiating the residual wax stream emerging from said dewaxer with near-infrared radiation;
    (c) determining the difference in optical absorptivity of said emerging stream at two selected wavelengths;
    (d) determining the weight percent isomerate oil from the difference in optical absorptivity;
    (e) controlling at least one of the operating parameters in response to said determined weight percent to optimize the dewaxing process.

11. The method of claim 10 wherein said two selected wavelengths are about 1210 nm and 1196 nm.

12. The method of claim 10 where said two selected wavelengths are about 927 nm and 916 nm.

13. A method for optimizing operating parameters for catalytic isomerization of a hydrocarbon feedstream comprising:
    (a) feeding a molten substantially waxy feedstream into one or more catalytic reactors with catalyst and hydrogen which under operating conditions isomerizes normal paraffins in said feedstream;
    (b) irradiating the stream emerging from said catalytic reactor with near-infrared radiation at two selected wavelengths;
    (c) determining the difference in optical absorptivity of said emerging stream at said two selected wavelengths;
    (d) determining the degree of isomerization from the difference in optical absorptivity; and
    (e) controlling at least one of the operating parameters in response to said determined degree of isomerization to optimize the catalytic isomerization.

14. The method of claim 13 wherein said two selected wavelengths are about 1210 nm and 1196 nm.

15. The method of claim 13 where said two selected wavelengths are about 927 nm and 916 nm.

16. The method for optimizing operating parameters of a dewaxing process comprising:
    (a) feeding a molten mixture of isomerate oil and wax feed into a dewaxer which under operating conditions separates the mixture into an isomerate oil stream and a residual wax stream;
    (b) irradiating the residual wax stream emerging from said dewaxer with near-infrared radiation;
    (c) determining the optical absorptivity of said emerging stream for at least one selected wavelength;
    (d) determining the weight percent isomeric oil from the optical absorptivity; and
    (e) controlling at least one of the operating parameters in response to said determined weight percent to optimize the dewaxing process.

17. The method of claim 16 wherein said method includes determining the optical absorptivity at a second selected wavelength, and determining the difference in the optical absorptivity between said two wavelengths.

18. The method of claim 17 wherein said two selected wave lengths are about 1210 nm and 1196 nm.

19. The method of claim 17 wherein said two selected wavelengths are about 927 nm and 916 nm.

* * * * *